US011207126B2

(12) United States Patent
Segit et al.

(10) Patent No.: US 11,207,126 B2
(45) Date of Patent: Dec. 28, 2021

(54) SMOKE EVACUATION ELECTROSURGICAL INSTRUMENT

(71) Applicant: Medtronic Advanced Energy LLC, Minneapolis, MN (US)

(72) Inventors: Alexander J. Segit, Eliot, ME (US); Jonathan J. Barry, Rochester, NH (US); Amy Bradley, Newton, NH (US); Peter Goodwin, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 356 days.

(21) Appl. No.: 16/040,742

(22) Filed: Jul. 20, 2018

(65) Prior Publication Data
US 2019/0021782 A1 Jan. 24, 2019

Related U.S. Application Data

(60) Provisional application No. 62/535,269, filed on Jul. 21, 2017.

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1206* (2013.01); *A61B 18/1477* (2013.01); *A61B 2018/00101* (2013.01); *A61B 2018/00107* (2013.01); *A61B 2018/00148* (2013.01); *A61B 2018/00601* (2013.01); *A61B 2018/00916* (2013.01); *A61B 2018/1412* (2013.01); *A61B 2218/008* (2013.01)

(58) Field of Classification Search
CPC . A61B 18/14; A61B 18/1477; A61B 18/1206; A61B 2018/00107; A61B 2018/00916; A61B 2018/00101; A61B 2018/00148; A61B 2018/00601; A61B 2018/1412; A61B 2218/008
USPC .......................................................... 606/41
See application file for complete search history.

(56) References Cited

U.S. PATENT DOCUMENTS

| 5,015,243 A | 5/1991 | Schifano |
| 5,409,484 A | 4/1995 | Erlich et al. |
| 5,431,650 A | 7/1995 | Cosmescu et al. |
| 5,451,223 A * | 9/1995 | Ben-Simhon ....... A61M 1/0084 604/35 |
| 5,830,214 A * | 11/1998 | Flom .................. A61B 18/1482 606/41 |

(Continued)

OTHER PUBLICATIONS

Written Opinion and International Search Report for PCT/US2018/043009 dated Nov. 21, 2018.

(Continued)

*Primary Examiner* — Linda C Dvorak
*Assistant Examiner* — Nils A Potter
(74) *Attorney, Agent, or Firm* — Patterson Thuente Pedersen, P.A.

(57) ABSTRACT

An electrosurgical instrument with smoke evacuation, having an electrode, a suction lumen, and a plurality of slots connected to suction lumen, in which the slots may be longer than they are wide and wider than they are thick. The electrosurgical instrument may have the slots arranged longitudinally about its central axis, and the suction lumen may be wider than the slot widths.

26 Claims, 7 Drawing Sheets

(56) References Cited

U.S. PATENT DOCUMENTS

| | | | |
|---|---|---|---|
| 5,836,944 A | 11/1998 | Cosmescu | |
| 7,357,802 B2 | 4/2008 | Palanker et al. | |
| 7,736,361 B2 | 6/2010 | Palanker et al. | |
| 2005/0090816 A1* | 4/2005 | McClurken | A61B 18/148 606/41 |
| 2009/0131932 A1* | 5/2009 | Vakharia | A61L 2/08 606/48 |
| 2009/0258590 A1 | 10/2009 | Prokash | |
| 2012/0150101 A1* | 6/2012 | Stearns | A61M 1/0031 604/24 |
| 2013/0006260 A1 | 1/2013 | Nakajima et al. | |
| 2015/0112323 A1 | 4/2015 | Hagg | |
| 2016/0157920 A1* | 6/2016 | Vayser | A61B 18/1402 600/249 |

OTHER PUBLICATIONS

International Preliminary Report on Patentability for PCT/US2018/043009 dated Jan. 30, 2020.

\* cited by examiner

SMOKE EVACUATION ELECTROSURGICAL INSTRUMENT

PRIORITY

This application claims the benefit of and priority to U.S. Provisional Application No. 62/535,269, filed Jul. 21, 2017, the entirety of which is incorporated herein by reference.

TECHNICAL FIELD

The present technology is generally related to smoke evacuation during electrosurgery. In addition, the disclosure relates to blockage resistant smoke evacuation in proximity to the electrode in an electrosurgical instrument.

BACKGROUND

Use of electrosurgical devices such as an electrosurgical instrument may generate smoke and debris such as eschar during surgery. It is desirable to continuously remove smoke generated during electrosurgery. This is sometimes accomplished by applying a vacuum at or near the electrosurgical site.

Smoke collection by means of suction is most effective when the suction aperture can be brought into close proximity with the point of smoke creation. With an electrosurgical instrument, this means providing smoke evacuation near the active electrode tip of the surgical instrument. This proximity increases the probability that tissue and eschar from the electrosurgery becomes stuck within the suction lumen, occluding it and stopping or reducing smoke evacuation. Users are commonly expected to clean the active tip of electrosurgical instruments and attempt to clear occlusions of the aperture. Small apertures or occlusions which occur downstream of the opening can be challenging to clear and may require additional time and effort, or may result in reduced smoke evacuation performance. It is desirable to provide smoke evacuation without the smoke evacuation apparatus being blocked with debris and while minimizing the distraction of manual intervention to clear clogged systems.

Two types of blockages are commonly observed. Large clumps are observed to block the opening of a suction lumen, and small clumps are observed to lodge inside and occlude the suction lumen. Both types of blockage frequently require manual unblocking, which prolongs surgery, distracts the surgical team, and may require introduction of tools such as gauze or brushes to the surgery. It is also desirable to remove smoke from the electrosurgical site without obscuring visibility, without requiring extra devices to be introduced to the surgical site, and without requiring that time and effort during surgery be devoted to correcting obstruction of the suction lumen. Smoke evacuation that is reliable, discreet, and low maintenance during surgery is desirable.

One way of preventing occlusion is to increase the size of the suction lumen and any connected apertures, which allows for the free passage of larger particles without clogging. This is a common solution as increasing the flowpath also increases the flowrate and contributes to the efficacy of smoke evacuation. Large equipment can obscure a surgeon's visibility and reduce the ability to access small anatomical features, particularly if the equipment is located in close proximity to the electrode. An increase in size of the suction lumen further downstream of the aperture can also create ergonomic challenges for a hand-held instrument.

The integration of smoke evacuation capabilities into electro-surgery has been occurring for quite some time. An example appears in U.S. Pat. No. 5,409,484A, which describes a basic handpiece architecture with suction.

US2009/0258590A1 describes hands-free smoke removal from an operative site through a tube connected to the operator's hand.

U.S. Pat. No. 5,451,223 describes an instrument with a tube providing suction close to a blade electrode, and a perforated plate near the blade.

U.S. Pat. No. 5,409,484A describes a filter with a tube for filtering material which passes through the tube.

U.S. Pat. No. 5,836,944A describes a removable shroud for use with an electro-surgical unit instrument where the shroud fits over a portion of the external surface of the electrosurgery unit instrument. The removable shroud includes a cylindrical shaped handpiece having an opening therein which provides means for accessing a hand switch contained on the electrosurgery unit instrument when the instrument is positioned within the shroud, a chute located alongside a bottom length of the cylindrical handpiece, and a tapered nozzle located near the distal ends of the cylindrical handpiece and the chute. The interior of the chute opens into the lumen of the cylindrical handpiece near the distal end of the chute and the proximal end of the chute extends beyond the proximal end of the cylindrical handpiece. This patent includes fins in the smoke pathway.

U.S. Pat. No. 5,431,650A describes an electrosurgical unit (ESU) apparatus is disclosed in which a handpiece and smoke evacuation shroud apparatus and method provides smoke collection without obstructing the surgeon's view of the surgical site through use of a smoke evacuation shroud design which controls the velocity and direction of the evacuating air flow in the vicinity of the surgical site by forming a vortex.

SUMMARY

Some aspects in accordance with principles of the present disclosure relate to an electrosurgical instrument with an electrode tip and a smoke evacuation system near the tip. The smoke evacuation system includes high-aspect-ratio slots designed to allow debris, tissue, or eschar build up to be easily cleared and to prevent downstream occlusions while maintaining a relatively small visual profile in close proximity to the electrosurgery site. In some embodiments, the active tip is a single pole electrode delivering radiofrequency energy.

The slots may have the following characteristics to realize these benefits: Slot width can be less than the minimum linear restriction of the remaining suction lumen cross-section. This prevents occlusions from forming within the suction lumen by ensuring that particles large enough to occlude the flow-path interior are "screened" out by the intervening surfaces between the slots, where they can be easily and quickly cleared during surgery. The surfaces forming the walls of the slots can be thinner than the width of the slots. This prevents a "tunneling" effect wherein particle agglomeration occurs along the slot side-walls. Slot length can be as long as possible to maximize each opening to achieve the highest possible flowrate and promote entrainment of small particles. This also minimizes the impact of clogs near the slots on totally smoke evacuation rate.

In one aspect, the present disclosure provides an electrosurgical instrument with smoke evacuation capability. Smoke evacuation is provided through at least one slot on the electrosurgical instrument near the electrode. The slots may be on a suction finger grip. The electrosurgical instrument has several slots that open to the suction lumen of the electrosurgical instrument, and then connect to a surgical vacuum system. The slots are longer than they are wide, and wider than they are thick. This design prevents clogging of the slots or suction lumen while allowing easy cleaning during surgery. The slots may be wider than the suction lumen's narrowest point, so that any particles that travel through the slots will be able to travel through the suction lumen without causing a clog. In some embodiments, each slot may be two to ten times longer than it is wide, and each slot may be at least one millimeter thick. In one embodiment, the slots are disposed longitudinally about the axis of the electrosurgical instrument. In other embodiments, the slots are arranged at angles or in other fashions, or may have other dimensions. Slots may be rectangular, oval, teardrop shaped, or other shapes.

Several features of the present disclosure provide features such as smoke removal, easy clearance of occlusions, prevention of internal occlusions, and clear visibility of the surgical site.

In one embodiment of the present disclosure, the electrosurgical instrument is designed for use by a robot rather than by a human. In another embodiment, the electrosurgical instrument includes a fiducial, electromagnetic coil, RFID element, or other devices for navigation or identification purposes.

The present disclosure uses a series of high-aspect ratio slots properly proportioned to prevent internal occlusions and allow eschar build up to be easily cleared while maintaining a high flow-rate and close proximity to the electrode.

DETAILED DESCRIPTION

Figure 1:
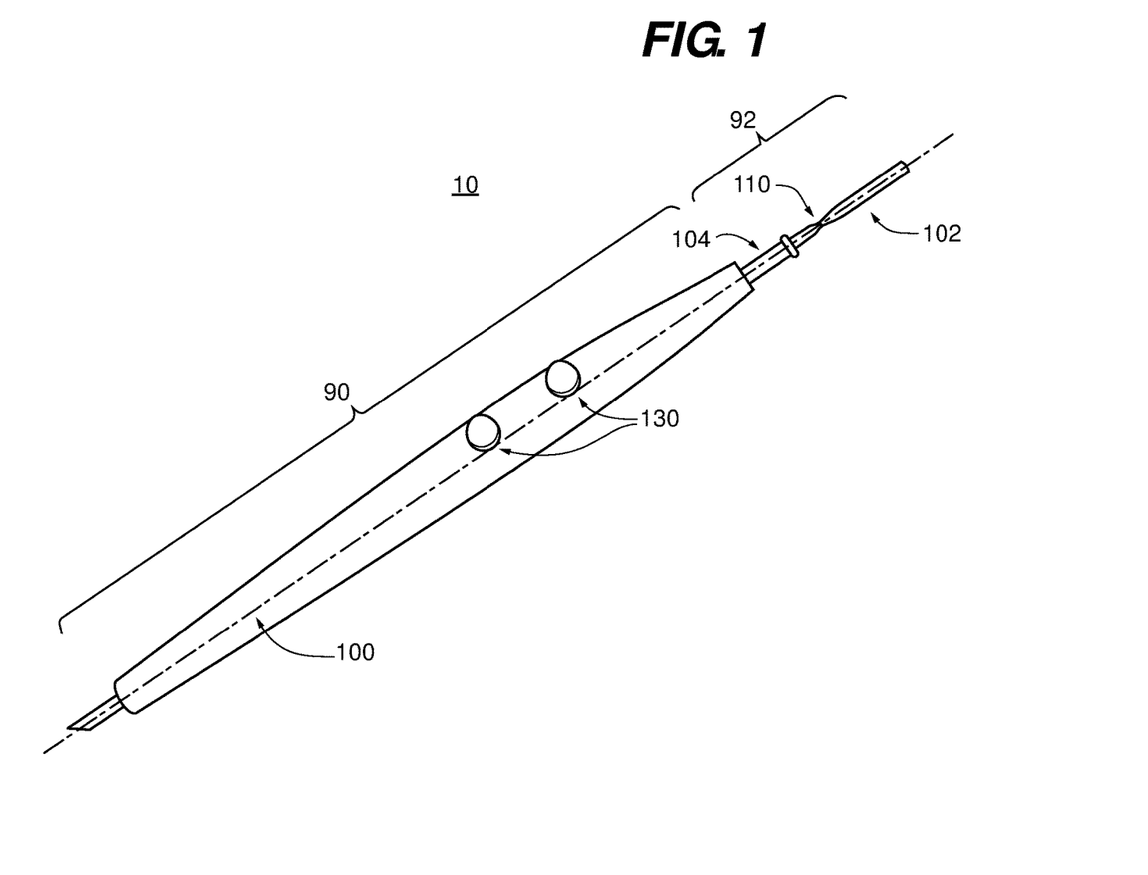
FIG. 1 depicts an electrosurgical instrument with smoke evacuation in accordance with an embodiment of the disclosure.

FIG. 1 depicts one embodiment of an electrosurgical instrument 10 with smoke evacuation, including a proximal portion 90, a distal portion 92, electrode 102, electrical conductor 110, and suction finger grip 104. In this embodiment, the electrical conductor 110 and the electrode 102 are different portions of the same electrically conductive object. Button 130 is shown, as is central axis 100. In this embodiment, electrosurgical instrument 10 is an electrosurgical pencil.

Figure 2:
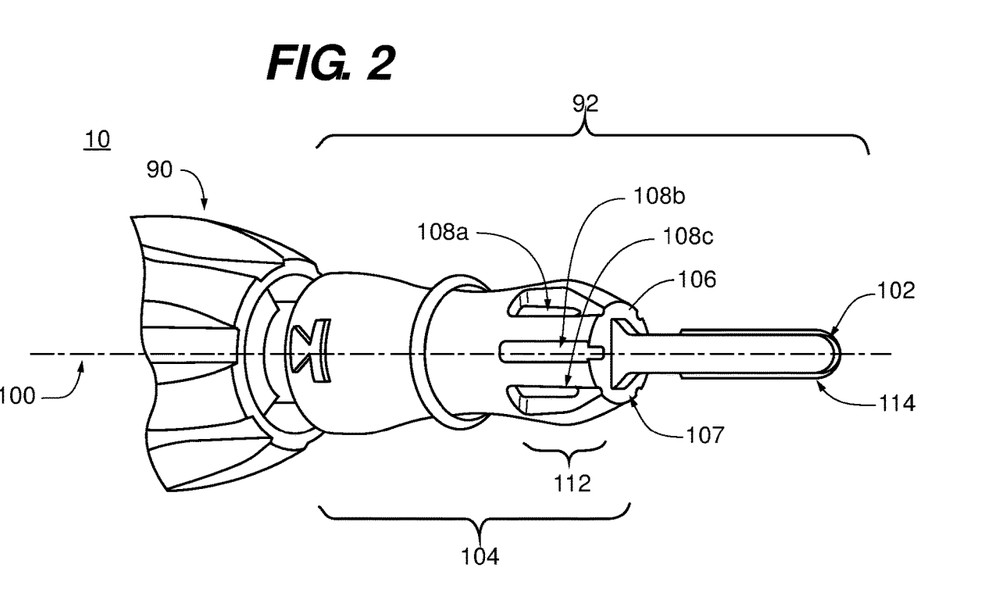
FIG. 2 is a close-in diagram showing the suction finger grip with high aspect-ratio slots and an electrode with a coating according to an embodiment.

FIG. 2 depicts one embodiment of the distal portion 92 of electrosurgical instrument 10, including the electrode 102 and suction finger grip 104 including handle port 106, aperture 112, and slots 108a, 108b, and 108c distributed longitudinally about central axis 100 and substantially parallel to central axis 100. Electrode 102 is partially within handle port 106 on distal face 107 in this embodiment. In this embodiment, distal face 107 is substantially flat and devoid of any openings, with handle port 106 sized such that it fits around electrode 102 with no air gap. Electrode 102 and electrical conductor 110 may be a single conductive monolith, or may be two different materials, or may have otherwise identical, similar, or different properties from one another. Proximal portion 90 is partially shown. In this embodiment, electrode 102 is paddle shaped and has a coating 114.

Figure 3:
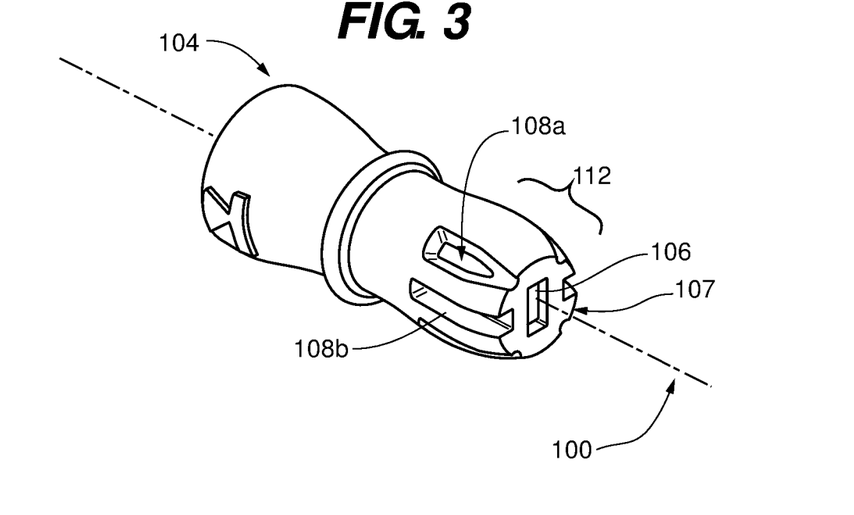
FIG. 3 is a close-in diagram showing the suction finger grip with high aspect-ratio slots according to an embodiment.

FIG. 3 depicts one embodiment of the suction finger grip 104 portion of the electrosurgical instrument 10 shown in FIG. 2, including handle port 106 in distal face 107, aperture 112, and slots 108a and 108b, which are disposed about central axis 100 longitudinally.

Figure 4:
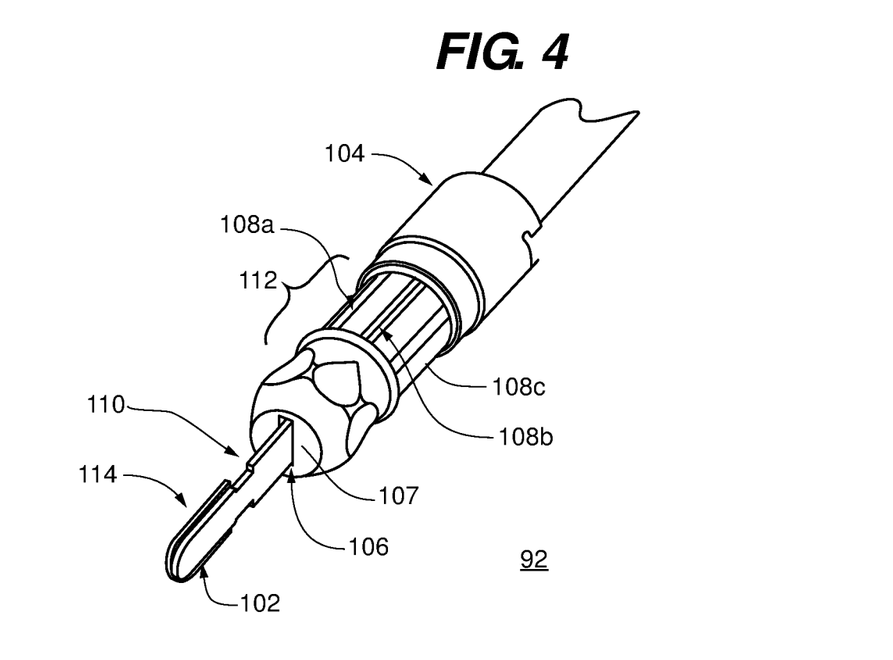
FIG. 4 is a close-in diagram showing the suction finger grip with high aspect-ratio slots and an electrode with a coating according to an embodiment.

FIG. 4 depicts one embodiment of the distal portion 92 of electrosurgical instrument 10, including the electrode 102, electrical conductor 110, and suction finger grip 104 including handle port 106, distal face 107, aperture 112, and slots 108a, 108b, and 108c. Slots 108a-c can be rectangular, or take other shapes such as but not limited to oval, triangle, or teardrop. In this embodiment, the electrical conductor 110 extends through handle port 106, and is a portion of the same electrically conductive monolith as the electrode 102. Either electrical conductor 110 or electrode 102 may be inside of handle port 106, and handle port 106 and electrical conductor 110 or electrode 102 may be sized relative to one another such that there is no gap between them, or there is some gap, or there may be a gap that is filled with a material such as a polymer, an epoxy, a glue, solder, or another substance. In this embodiment, distal face 107 is substantially flat, free of any air gaps, and able to act as a stop surface or barrier to limit insertion of electrosurgical instrument 10 into a body. In this embodiment, the electrode 102 has a coating 114. Electrode 102 and electrical conductor 110 are flattened in this embodiment, but can be arranged in many different shapes including flattened, sharpened blade, round, triangular, angled, pointed, hook, sphere, cylindrical, diamond, loop, and others. Suction finger grip 104 can be in many different shapes, and aperture 112 can be positioned in many different locations in suction finger grip 104. Coating 114 can be a variety of materials, including but not limited to an elastomeric coating, glass, zirconia, silicon nitride, aluminum oxide, boron nitride, silicon dioxide, zirconium oxide, titanium nitride, gold, silver, nitinol, platinum, palladium, iridium, a polymer, alloys, silicone, ceramic, and stainless steel; or coating 114 may be as described in U.S. Pat. No. 7,357,802 or 7,736,361, the disclosures of which are hereby incorporated by reference herein in their entirety. Electrical conductor 110 can be made from a variety of materials, and may be surrounded by an electrical or thermal insulator partly or fully. Electrical conductor 110 may be made from the same material as electrode 102 or a different material. Possible materials for electrode 102 or electrical conductor 110 include but are not limited to stainless steel, gold, silver, nitinol, platinum, palladium, iridium, copper, or alloys. Electrode 102 may be sized long and thin such as for arthroscopic surgery, or electrical conductor 110 may extended far beyond handle port 106, for instance for arthroscopic surgery. Electrode 102 may extend far inside of electrosurgical instrument 10.

Figure 5:
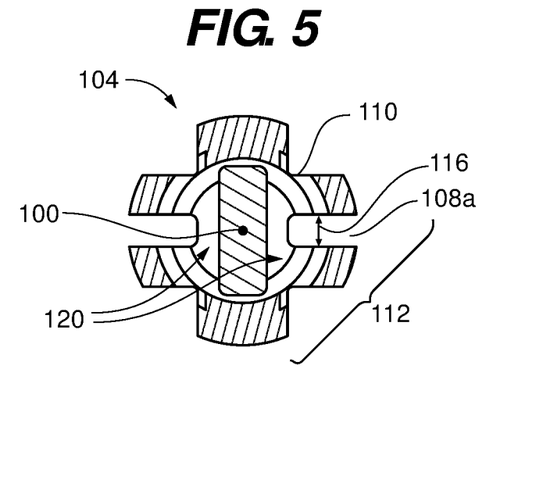
FIG. 5 is a cross-section viewed along the longitudinal axis, showing the suction finger grip according to an embodiment.

FIG. 5 depicts one embodiment of the disclosure as a cross-sectional view of suction finger grip 104 shown in FIG. 3, looking along central axis 100 at aperture 112. Electrical conductor 110 divides suction lumen 120 in half. Slot 108a has a slot width 116.

Figure 6:
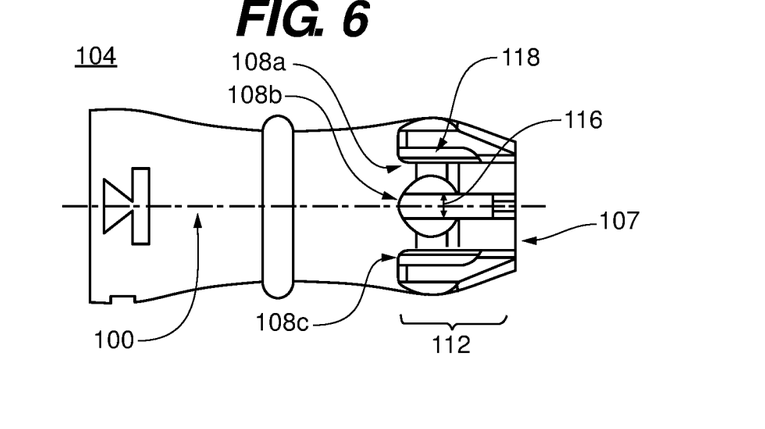
FIG. 6 is external view viewed perpendicular to the longitudinal axis, showing the suction finger grip according to an embodiment.

FIG. 6 depicts one embodiment of the disclosure as an external side view of suction finger grip 104 shown in FIG. 3. Aperture 112 with slots 108a, 108b, 108c is shown, including slot width 116 of slot 108b and slot length 118 of slot 108a. Distal face 107 is shown. Every slot 108a-c may have its own width and length. It is possible that, in addition to the slots, some embodiments of the present disclosure could have additional openings with different dimensions. Slot length 118 is greater than slot width 116, and may be greater than a 1:1 ratio or in the range from a 2:1 ratio to a 10:1 ratio.

Figure 7:
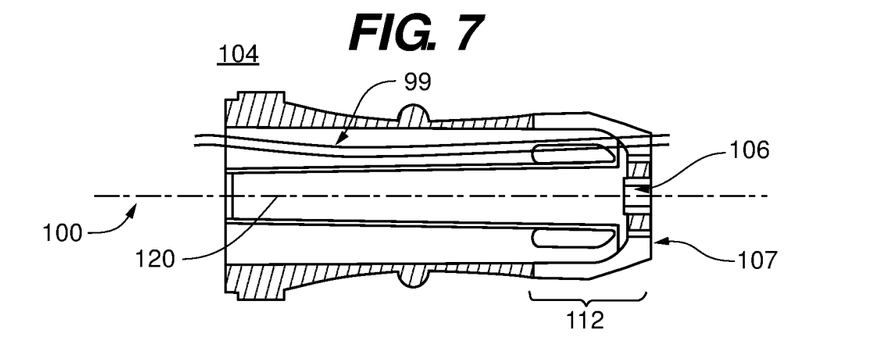
FIG. 7 is a cross-section viewed perpendicular to the longitudinal axis, showing the suction finger grip according to an embodiment.

FIG. 7 depicts one embodiment of the disclosure, a cross-sectional side view of suction finger grip 104 shown in FIG. 3. Aperture 112 is shown, as is handle port 106 in distal face 107 and suction lumen 120. Electrical conductor 110 and electrode 102 are not present in FIG. 7. The electrode 102 may be designed for surgery with gas such as argon, and a gas supply line 99 may be included. Supply lines for other gases may be provided in some embodiments, and other gases used during surgery. Central axis 100 is shown.

Figure 8:
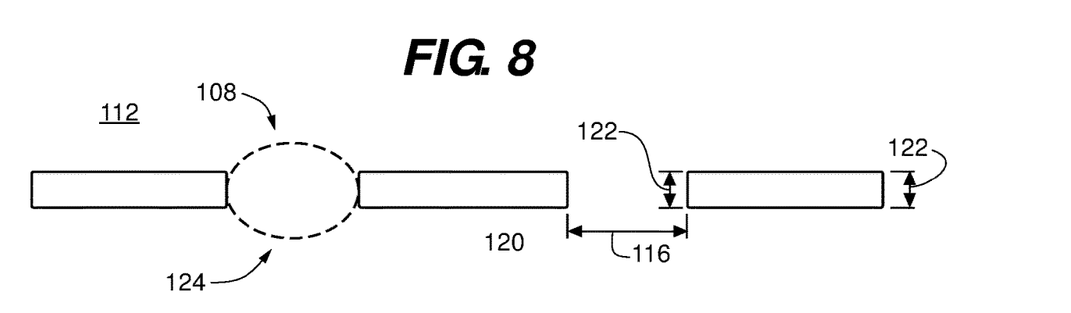
FIG. 8 depicts a cross-sectional view along the longitudinal axis of one embodiment of a portion of the suction finger grip.

FIG. 8 depicts a cross-sectional view of one embodiment of a portion of the aperture 112, looking in a direction parallel to central axis 100. Slot width 116 and slot thickness 122 are shown. Sloth width 116 is greater than slot thickness 122, meaning that particulate 124 will be easily pulled through slot 108 into suction lumen 120.

Figure 9:
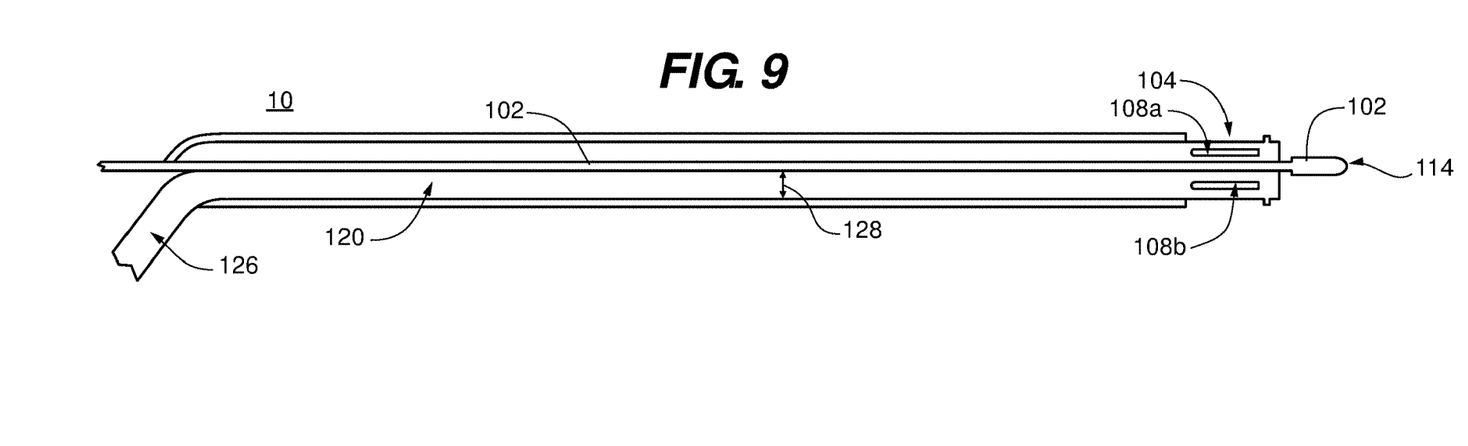
FIG. 9 is a cross-section of the electrosurgical instrument of the present disclosure viewed perpendicular to the longitudinal axis.

FIG. 9 depicts a cross-sectional view of one embodiment of electrosurgical instrument 10, looking in a direction perpendicular to the electrode 102. Suction lumen 120 is shown with a minimum linear restriction 128 in its narrowest portion. Suction line 126 is shown connected to suction lumen 120. Suction line 126 connects to a vacuum source (not pictured) in the surgical theatre. Coating 114 is shown on electrode 102, and suction finger grip 104 is disposed about electrode 102, with slots 108a and 108b distributed longitudinally. Slots 108a, 108b are in fluid communication with suction lumen 120, as gas, liquids, smoke, or debris can travel via suction through slots 108a and 108b into suction lumen 120, then through suction line 126. Slot width 116 (not pictured in this figure) is less that minimum linear restriction 128.

Figure 10:
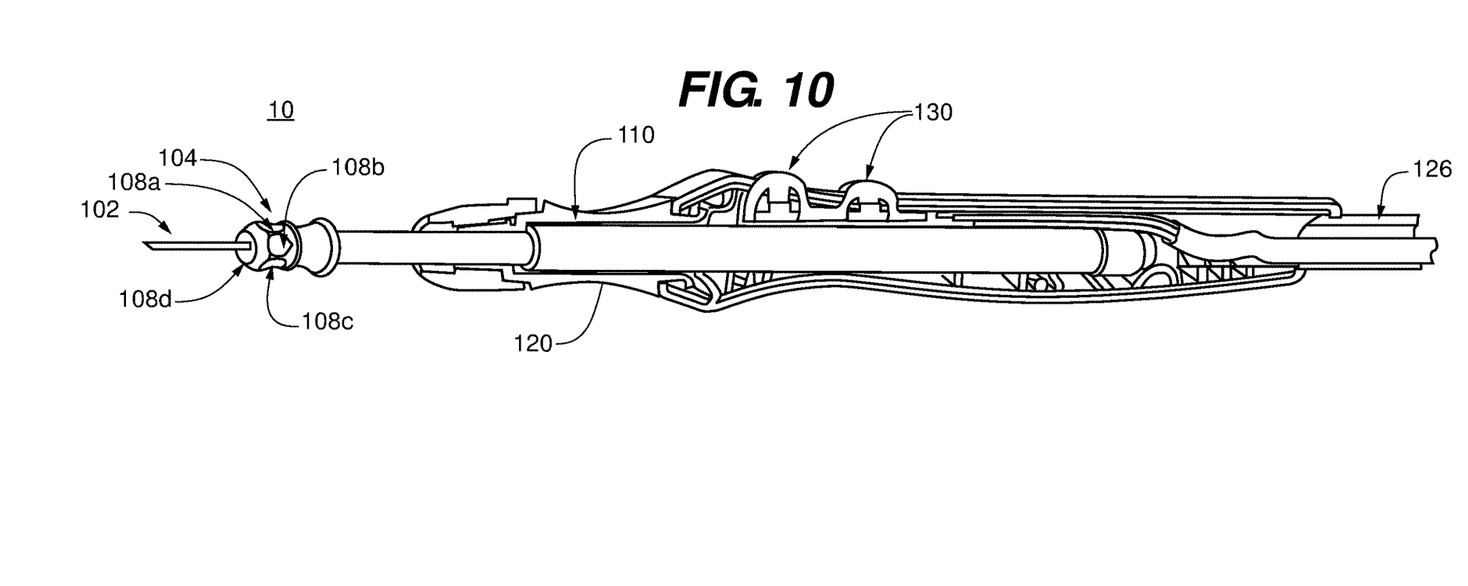
FIG. 10 is a cross-section of the electrosurgical instrument of present disclosure.

FIG. 10 depicts a cross-sectional view of one embodiment of electrosurgical instrument 10. In this embodiment, suction lumen 120 is defined by electrical conductor 110, which takes the form of a hollow tube of conductive material through much of electrosurgical instrument 10 before connecting to suction finger grip 104 and electrode 102. Suction line 126 is shown connected to suction lumen 120. Suction line 126 connects to a suction source 132 (not pictured) in the surgical theatre. Suction finger grip 104 is disposed about electrode 102, with slots 108a, 108b, 108c, and 108d distributed longitudinally. Button 130 is shown.

Figure 11:
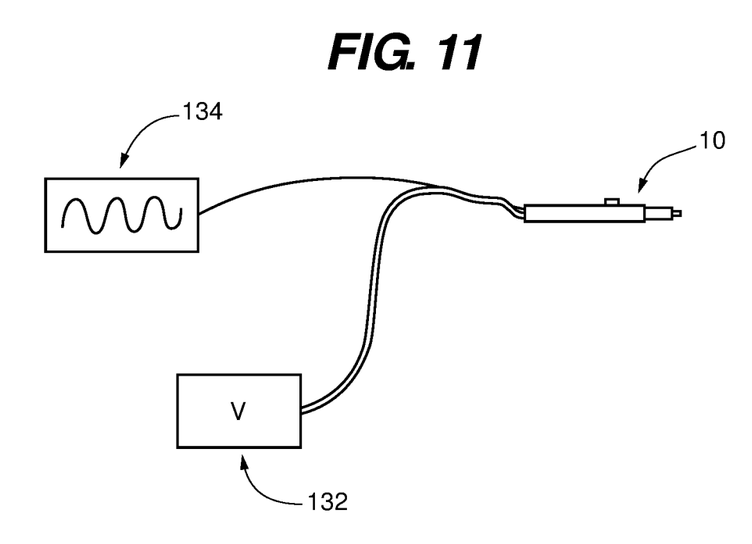
FIG. 11 depicts an embodiment of the present disclosure with a radiofrequency generator, suction source, and electrosurgical instrument.

FIG. 11 depicts one embodiment of the present disclosure, in which electrosurgical instrument 10 is connected to radiofrequency generator 134 and suction source 132. Suction source 132 may be a surgical pump, surgical vacuum, vacuum pump, gas pump, or other devices.

What is claimed is:

1. An electrosurgical instrument with smoke evacuation, comprising:
a suction lumen having a minimum linear restriction;
a plurality of slots disposed longitudinally about a central axis of the electrosurgical instrument; and
an electrode arranged along the central axis of the electrosurgical instrument,
wherein the suction lumen is in fluid communication with the slots,
wherein each slot has a pair of slot side-walls disposed longitudinally about a central axis of the electrosurgical instrument defining a slot thickness, a slot length, and a slot width, wherein the pair of slot side-walls of at least one slot of the plurality of slots are oriented orthogonal to one another, and the pair of slot side-walls of at least one other slot of the plurality of slots are oriented parallel to one another,
wherein each slot length is greater than the corresponding slot width,
wherein each slot width is greater than the corresponding slot thickness,
wherein at least one slot of the plurality of slots is disposed on both a distal face and longitudinally about the central axis of the electrosurgical instrument, and
wherein the minimum linear restriction is greater than each slot width.

2. The electrosurgical instrument of claim 1, wherein each slot length is between two and ten times greater than the corresponding slot width.

3. The electrosurgical instrument of claim 2, wherein each slot thickness is at least 1 millimeter.

4. The electrosurgical instrument of claim 1, further comprising ABS plastic.

5. The electrosurgical instrument of claim 1, wherein the electrode comprises stainless steel.

6. The electrosurgical instrument of claim 5, wherein the electrode further comprises a coating.

7. The electrosurgical instrument of claim 6, wherein the coating comprises a ceramic.

8. The electrosurgical instrument of claim 1, wherein the electrode comprises a cutting edge.

9. The electrosurgical instrument of claim 1, wherein the electrode is paddle shaped.

10. The electrosurgical instrument of claim 1, further comprising a gas supply line.

11. The electrosurgical instrument of claim 1, wherein the electrosurgical instrument is an electrosurgical pencil.

12. An electrosurgical system, comprising:
a suction source;
a radiofrequency generator; and
an electrosurgical instrument, the electrosurgical instrument comprising:
an electrode,
a distal face free of an air gap,
a suction lumen having a minimum linear restriction, and
a plurality of slots disposed longitudinally about a central axis of the electrosurgical instrument, wherein the suction lumen is in fluid communication with the slots, wherein each slot has a pair of slot side-walls disposed longitudinally about a central axis of the electrosurgical instrument defining a slot thickness, a slot length, and a slot width, wherein the pair of slot side-walls of at least one slot of the plurality of slots are oriented orthogonal to one another, and the pair of slot side-walls of at least one other slot of the plurality of slots are oriented parallel to one another, wherein each slot length is greater than the corresponding slot width, wherein each slot width is greater than the corresponding slot thickness, wherein at least one slot of the plurality of slots is disposed on both a distal face and longitudinally about the central axis of the electrosurgical instrument, and wherein the minimum linear restriction is greater than each slot width.

13. The electrosurgical instrument of claim 12, further comprising ABS plastic.

14. The electrosurgical instrument of claim 12, wherein the electrode comprises stainless steel.

15. The electrosurgical instrument of claim 14, wherein the electrode further comprises a coating.

16. The electrosurgical instrument of claim 15, wherein the coating comprises a ceramic.

17. The electrosurgical instrument of claim 12, wherein the electrode comprises a cutting edge.

18. The electrosurgical instrument of claim 12, wherein the electrode is paddle shaped.

19. The electrosurgical instrument of claim 12, wherein the electrosurgical instrument is an electrosurgical pencil.

20. The electrosurgical instrument of claim 12, further comprising a gas supply line.

21. An electrosurgical instrument with smoke evacuation, comprising:
 a central axis;
 an electrode arranged along the central axis;
 a suction lumen having a minimum linear restriction, and
 a plurality of slots disposed longitudinally about the central axis of the electrosurgical instrument, wherein the electrosurgical instrument is an electrosurgical pencil, wherein the suction lumen is in fluid communication with the slots, wherein each slot has a pair of slot side-walls disposed longitudinally about a central axis of the electrosurgical instrument defining a slot thickness, a slot length, and a slot width, wherein the pair of slot side-walls of at least one slot of the plurality of slots are oriented orthogonal to one another, and the pair of slot side-walls of at least one other slot of the plurality of slots are oriented parallel to one another, wherein each slot length is greater than the corresponding slot width, wherein each slot width is greater than the corresponding slot thickness, wherein each slot length is substantially parallel to the central axis, wherein at least one slot of the plurality of slots traverses a corner to be disposed on both a distal face and longitudinally, substantially parallel to the central axis of the electrosurgical instrument, wherein each slot length is between two and ten times greater than the corresponding slot width, and wherein the minimum linear restriction of the suction lumen is greater than each slot width.

22. The electrosurgical instrument of claim 21, wherein each slot thickness is at least 1 millimeter.

23. The electrosurgical instrument of claim 21, further comprising a distal face free of an air gap.

24. The electrosurgical instrument of claim 21, wherein the electrode comprises a cutting edge.

25. The electrosurgical instrument of claim 21, wherein the electrode is a paddle electrode.

26. The electrosurgical instrument of claim 21, wherein the cross-section of the instrument is triangular.

* * * * *